United States Patent

Finch et al.

[11] Patent Number: 5,810,798
[45] Date of Patent: Sep. 22, 1998

[54] ABSORBENT ARTICLE HAVING A THIN, EFFICIENT ABSORBENT CORE

[75] Inventors: Valerie Victoria Finch; Rebecca Lyn Dilnik, both of Neenah; Mary Watt Goggans, Appleton; Janet Jessie Larsen, Neenah; Kim LaRae Resheski-Wedepohl, Reedsville, all of Wis.

[73] Assignee: Kimberly-Clark Worldwide, Inc., Neenah, Wis.

[21] Appl. No.: 784,113

[22] Filed: Jan. 15, 1997

Related U.S. Application Data

[63] Continuation-in-part of Ser. No. 475,324, Jun. 30, 1995, abandoned.

[51] Int. Cl.$^6$ .............................. A61F 13/15; A61F 13/20
[52] U.S. Cl. ...................... 604/378; 604/385.1; 428/172
[58] Field of Search .................................. 604/378, 384, 604/385.1, 379, 380, 381, 382, 383; 428/156, 172, 98

[56] References Cited

U.S. PATENT DOCUMENTS

| | | |
|---|---|---|
| 1,863,333 | 6/1932 | Heitmeyer . |
| 1,910,872 | 5/1933 | Williams . |
| 2,047,054 | 7/1936 | Beyer, Jr. ................ 128/290 |
| 2,295,016 | 9/1942 | Scribner ................. 128/290 |
| 2,295,439 | 9/1942 | Voigtman ............... 128/284 |
| 2,468,876 | 5/1949 | Hermanson ............ 128/290 |
| 2,564,689 | 8/1951 | Harwood et al. ...... 128/290 |
| 2,582,344 | 1/1952 | Milton .................... 128/290 |
| 2,772,678 | 12/1956 | Leupold ................. 128/290 |
| 2,787,271 | 4/1957 | Clark ...................... 128/290 |
| 2,833,283 | 5/1958 | Spahr et al. ........... 128/290 |
| 2,900,980 | 8/1959 | Harwood ................ 128/290 |
| 2,960,089 | 11/1960 | Harwood et al. ...... 128/290 |
| 3,067,747 | 12/1962 | Wolterding et al. ... 128/296 |
| 3,073,308 | 1/1963 | Stamberger ............ 128/287 |

(List continued on next page.)

FOREIGN PATENT DOCUMENTS

| | | |
|---|---|---|
| 0 234 194 B1 | 9/1987 | European Pat. Off. . |
| 0 272 683 A2 | 6/1988 | European Pat. Off. . |
| 0 470 392 A1 | 2/1992 | European Pat. Off. . |
| 1-122727 | 8/1989 | Japan . |
| 2-168950 | 6/1990 | Japan . |
| 1 333 081 | 10/1973 | United Kingdom . |
| 2 111 836 | 7/1983 | United Kingdom . |
| 2 124 907 | 2/1984 | United Kingdom . |
| 2 165 757 | 4/1986 | United Kingdom . |
| 2 180 162 | 3/1987 | United Kingdom . |
| 2 258 403 | 2/1993 | United Kingdom . |
| 2 258 840 | 2/1993 | United Kingdom . |
| 2 266 464 | 11/1993 | United Kingdom . |
| WO 91/00719 | 1/1991 | WIPO . |
| WO 91/11163 | 8/1991 | WIPO . |
| WO 93/09745 | 5/1993 | WIPO . |

*Primary Examiner*—Robert A. Clarke
*Assistant Examiner*—Ki Yong O
*Attorney, Agent, or Firm*—Thomas J. Connelly

[57] ABSTRACT

Disclosed is an absorbent article having an absorbent core. The absorbent core includes a primary absorbent member and a secondary absorbent member. The primary absorbent member has a fluid distribution rate, expressed as the ratio of a stain area in the primary absorbent member to a stain area in the secondary absorbent member, along a X-Y direction greater than about 1.8 times faster than the secondary absorbent member. The fluid distribution rate is expressed as a ratio of a stain area in the primary absorbent member to a stain area in the secondary absorbent member five minutes after a given volume of test fluid insults the absorbent core. The secondary absorbent member has a substantial portion thereof composed of a non-absorbent polymeric composition. The secondary absorbent member is superposed over a portion of the primary absorbent member. In a preferred embodiment, the secondary absorbent member has an aperture or orifice having an open surface area greater than about 20% of the secondary absorbent member surface area.

20 Claims, 2 Drawing Sheets

U.S. PATENT DOCUMENTS

| | | | |
|---|---|---|---|
| 3,088,463 | 5/1963 | Harmon | 128/290 |
| 3,143,113 | 8/1964 | Mills | 128/290 |
| 3,343,543 | 9/1967 | Glassman | 128/290 |
| 3,344,789 | 10/1967 | Arnold et al. | 128/287 |
| 3,375,827 | 4/1968 | Bletzinger et al. | 128/290 |
| 3,397,697 | 8/1968 | Rickard | 128/288 |
| 3,403,681 | 10/1968 | Hoey et al. | 128/290 |
| 3,441,023 | 4/1969 | Rijssenbeek | 128/287 |
| 3,463,154 | 8/1969 | Hendricks | 128/287 |
| 3,477,433 | 11/1969 | Dillon | 128/290 |
| 3,525,337 | 8/1970 | Simons et al. | 128/290 |
| 3,545,442 | 12/1970 | Wicker et al. | 128/296 |
| 3,589,956 | 6/1971 | Kranz et al. | 156/62.4 |
| 3,593,717 | 7/1971 | Jones, Sr. | 128/290 |
| 3,654,060 | 4/1972 | Goldman | 161/112 |
| 3,654,929 | 4/1972 | Nilsson et al. | 128/287 |
| 3,667,468 | 6/1972 | Nystrand et al. | 128/290 |
| 3,699,966 | 10/1972 | Chapuis | 128/290 R |
| 3,746,592 | 7/1973 | Nystrand et al. | 156/202 |
| 3,749,627 | 7/1973 | Jones, Sr. | 156/268 |
| 3,759,262 | 9/1973 | Jones, Sr. | 128/290 R |
| 3,771,525 | 11/1973 | Chapuis | 128/290 R |
| 3,865,112 | 2/1975 | Roeder | 128/290 R |
| 3,886,941 | 6/1975 | Duane et al. | 128/287 |
| 3,888,256 | 6/1975 | Studinger | 128/296 |
| 3,929,135 | 12/1975 | Thompson | 128/287 |
| 3,932,322 | 1/1976 | Duchane | 260/17.4 GC |
| 3,939,838 | 2/1976 | Fujinami et al. | 128/290 R |
| 3,945,386 | 3/1976 | Anczurowski et al. | 128/287 |
| 3,954,107 | 5/1976 | Chesky et al. | 128/290 R |
| 3,965,906 | 6/1976 | Karami | 128/287 |
| 3,967,623 | 7/1976 | Butterworth et al. | 128/287 |
| 3,994,299 | 11/1976 | Karami | 128/287 |
| 4,014,341 | 3/1977 | Karami | 128/287 |
| 4,029,101 | 6/1977 | Chesky et al. | 128/290 R |
| 4,037,602 | 7/1977 | Hawthorne | 128/287 |
| 4,057,061 | 11/1977 | Ishikawa et al. | 128/284 |
| 4,069,822 | 1/1978 | Buell | 128/294 |
| 4,079,739 | 3/1978 | Whitehead | 128/290 R |
| 4,100,324 | 7/1978 | Anderson et al. | 428/288 |
| 4,195,634 | 4/1980 | DiSalvo et al. | 128/290 R |
| 4,223,677 | 9/1980 | Anderson | 128/287 |
| 4,232,674 | 11/1980 | Melican | 128/287 |
| 4,276,338 | 6/1981 | Ludwa et al. | 428/137 |
| 4,285,343 | 8/1981 | McNair | 128/287 |
| 4,315,507 | 2/1982 | Whitehead et al. | 128/287 |
| 4,323,068 | 4/1982 | Aziz | 128/287 |
| 4,323,069 | 4/1982 | Ahr et al. | 128/287 |
| 4,324,246 | 4/1982 | Mullane et al. | 128/287 |
| 4,327,731 | 5/1982 | Powell | 128/287 |
| 4,338,371 | 7/1982 | Dawn et al. | 428/283 |
| 4,357,939 | 11/1982 | Jackson et al. | 128/290 R |
| 4,372,312 | 2/1983 | Fendler et al. | 128/290 R |
| 4,397,644 | 8/1983 | Matthews et al. | 604/378 |
| 4,411,660 | 10/1983 | Dawn et al. | 604/396 |
| 4,433,972 | 2/1984 | Malfitano | 604/385 |
| 4,507,121 | 3/1985 | Leung | 604/361 |
| 4,531,945 | 7/1985 | Allison | 604/378 |
| 4,540,414 | 9/1985 | Wishman | 604/378 |
| 4,551,142 | 11/1985 | Kopolow | 604/368 |
| 4,589,876 | 5/1986 | Van Tilburg | 604/385 R |
| 4,608,047 | 8/1986 | Mattingly | 604/387 |
| 4,623,340 | 11/1986 | Luceri | 604/385 R |
| 4,626,254 | 12/1986 | Widlund et al. | 604/383 |
| 4,627,848 | 12/1986 | Lassen et al. | 604/370 |
| 4,629,643 | 12/1986 | Curro et al. | 428/131 |
| 4,631,062 | 12/1986 | Lassen et al. | 604/385 R |
| 4,636,209 | 1/1987 | Lassen | 604/378 |
| 4,676,786 | 6/1987 | Nishino | 604/378 |
| 4,687,478 | 8/1987 | Van Tilburg | 604/387 |
| 4,690,679 | 9/1987 | Mattingly, III et al. | 604/383 |
| 4,699,620 | 10/1987 | Bernardin | 604/385 A |
| 4,705,513 | 11/1987 | Sheldon et al. | 604/361 |
| 4,710,186 | 12/1987 | DeRossett et al. | 604/383 |
| 4,731,071 | 3/1988 | Pigneul | 604/385 R |
| 4,738,674 | 4/1988 | Todd et al. | 604/361 |
| 4,741,941 | 5/1988 | Englebert et al. | 428/71 |
| 4,755,413 | 7/1988 | Morris | 428/138 |
| 4,755,905 | 7/1988 | Molee et al. | 604/478 |
| 4,781,962 | 11/1988 | Zamarripa et al. | 428/138 |
| 4,798,601 | 1/1989 | Shirose et al. | 604/368 |
| 4,798,603 | 1/1989 | Meyer et al. | 604/378 |
| 4,798,604 | 1/1989 | Carter | 604/383 |
| 4,806,411 | 2/1989 | Mattingly, III et al. | 428/139 |
| 4,822,668 | 4/1989 | Tanaka et al. | 428/283 |
| 4,846,813 | 7/1989 | Raley | 604/385.1 |
| 4,846,824 | 7/1989 | Lassen et al. | 604/385.1 |
| 4,880,419 | 11/1989 | Ness | 604/368 |
| 4,886,632 | 12/1989 | Van Iten et al. | 264/156 |
| 4,892,534 | 1/1990 | Datta et al. | 604/370 |
| 4,895,749 | 1/1990 | Rose | 428/132 |
| 4,908,026 | 3/1990 | Sukiennik et al. | 604/378 |
| 4,938,756 | 7/1990 | Salek | 604/368 |
| 4,950,264 | 8/1990 | Osborn, III | 604/385.1 |
| 4,963,139 | 10/1990 | Dabroski | 604/378 |
| 4,973,325 | 11/1990 | Sherrod et al. | 604/368 |
| 4,988,344 | 1/1991 | Reising et al. | 604/368 |
| 4,988,345 | 1/1991 | Reising | 604/368 |
| 5,009,653 | 4/1991 | Osborn, III | 604/385.1 |
| 5,013,309 | 5/1991 | Baigas, Jr. et al. | 604/368 |
| 5,037,409 | 8/1991 | Chen et al. | 604/358 |
| 5,037,412 | 8/1991 | Tanzer et al. | 604/359 |
| 5,048,589 | 9/1991 | Cook et al. | 162/109 |
| 5,125,918 | 6/1992 | Seidy | 604/386 |
| 5,134,007 | 7/1992 | Reising et al. | 428/78 |
| 5,135,521 | 8/1992 | Luceri et al. | 604/383 |
| 5,188,625 | 2/1993 | Van Iten et al. | 604/383 |
| 5,201,727 | 4/1993 | Nakanishi et al. | 604/390 |
| 5,219,341 | 6/1993 | Serbiak et al. | 604/361 |
| 5,248,309 | 9/1993 | Serbiak et al. | 604/368 |
| 5,257,982 | 11/1993 | Cohen et al. | 604/378 |
| 5,294,478 | 3/1994 | Wanek et al. | 428/218 |
| 5,300,054 | 4/1994 | Feist et al. | 604/378 |
| 5,300,055 | 4/1994 | Buell | 604/385.1 |
| 5,304,161 | 4/1994 | Noel et al. | 604/378 |
| 5,330,457 | 7/1994 | Cohen | 604/378 |
| 5,348,547 | 9/1994 | Payne et al. | 604/378 |
| 5,356,405 | 10/1994 | Thompson et al. | 604/384 |
| 5,368,926 | 11/1994 | Thompson et al. | 428/284 |
| 5,370,764 | 12/1994 | Alikhan | 156/553 |
| 5,382,400 | 1/1995 | Pike et al. | 264/168 |
| 5,399,412 | 3/1995 | Sudall et al. | 428/153 |
| 5,415,640 | 5/1995 | Kirby et al. | 604/383 |
| 5,423,787 | 6/1995 | Kjellberg | 604/368 |
| 5,423,788 | 6/1995 | Rollins et al. | 604/385.1 |
| 5,429,629 | 7/1995 | Latimer et al. | 604/378 |
| 5,429,630 | 7/1995 | Beal et al. | 604/385.1 |
| 5,437,653 | 8/1995 | Gilman et al. | 604/378 |
| 5,439,458 | 8/1995 | Noel et al. | 604/378 |
| 5,454,800 | 10/1995 | Hirt et al. | 604/378 |
| 5,533,991 | 7/1996 | Kirby et al. | 604/383 |
| 5,609,588 | 3/1997 | DiPalma et al. | 604/369 |
| 5,611,879 | 3/1997 | Morman | 156/201 |

ABSORBENT ARTICLE HAVING A THIN, EFFICIENT ABSORBENT CORE

This application is a continuation-in-part of U.S. patent application Ser. No. 08/475,324 filed Jun. 30, 1995, now abandoned.

FIELD OF THE INVENTION

This invention relates to disposable absorbent articles and particularly to sanitary napkins containing multiple layers of absorbent. More particularly, this invention relates to absorbent cores having improved wicking capability along an X-Y plane.

BACKGROUND OF THE INVENTION

Generally, disposable absorbent articles include, in their construction, an absorbent core positioned between a liquid-permeable cover and a liquid-impermeable baffle. The cover material is generally designed to allow body exudates to permeate through the cover so that the absorbent core can absorb the fluids. The baffle material is generally fluid impermeable and is positioned so that it is away from the body. As used herein, the term "absorbent articles" refers to products such as diapers, sanitary napkins, training pants, incontinent garments, overnight pads, panty liners, underarm shields, as well as other absorbent devices used for medical purposes such as surgical absorbents. Such articles are designed to absorb body fluids, such as urine, menses, blood, perspiration and other excrement discharged by the body. For purposes of clarity and illustration only, the embodiments described herein will be in the form of a sanitary napkin, also referred to as catamenial pads, feminine pads, overnight pads, panty liners, and panty shields which are designed to be worn by a woman to absorb menses and other body fluids discharged before, during, and after a menstrual period. Such products are external devices which typically are held in position by a garment adhesive or by mechanical attachment to an adjacent undergarment.

One continuing problem in the formation of absorbent articles is that the bodily excretions are usually directed at one portion of the absorbent pad, whereas the absorptive capacity is spread over a greater area. In a conventional sanitary napkin made of multiple layers of cellulosic material, when fluid is absorbed by the wood pulp fluff or similar cellulosic material, the capillary walls tend to collapse inward. This collapse prevents fluid from being conducted downward and substantially diminishes the inherent resiliency of the cellulosic material.

This may create an early failure problem as the fluid to be absorbed cannot be efficiently spread through the absorbent. If the fluid does not spread throughout the absorbent, it may run off the edge of the saturated zone.

A related problem is that after the capillaries collapse, fluid which would normally be conducted downward tends to remain at or near the top surface of the napkin. This contributes to the phenomenon known as rewet where the fluid is desorbed and contacts the wearer, or contributes to fluid failing to penetrate the cover providing a wet, uncomfortable napkin surface.

Now an absorbent article has been invented which utilizes an absorbent having a high wicking ability, especially for menses, as well as providing post-use visual signals to the user that the absorbent capacity of the sanitary napkin is being fully utilized.

SUMMARY OF THE INVENTION

Briefly, this invention relates to absorbent articles, such as diapers, training pants, incontinent garments, overnight pads, panty liners, underarm shields and sanitary napkins. For purposes of description only, the preferred embodiment is described as a sanitary napkin which are designed to absorb menstrual fluid and other excrements discharged by the body during a menstrual period. Accordingly, the absorbent article of this invention includes an absorbent core having a primary absorbent member and a secondary absorbent member. The secondary absorbent member is superposed over at least a portion of the primary absorbent member and can be positioned so as to be in a face-to-face relationship with the primary absorbent member. The secondary absorbent member contains a substantial amount of a nonabsorbent polymeric composition which conventionally are thermoplastics. The primary absorbent member, which is an uncreped throughdried towel, has a fluid distribution rate along a X-Y direction, greater than about 1.8 times faster than the secondary absorbent member. The fluid distribution rate is expressed as the ratio of the stain area in the primary absorbent member to the stain area in the secondary absorbent member after 5 minutes for a predetermined amount of fluid insulting the absorbent core.

The general object of this invention is to provide an absorbent article for absorbing body fluids such as urine, menses, blood, etc. A more specific object of this invention is to provide an absorbent article having at least two absorbent members wherein the primary absorbent member has a greater wicking rate along an X-Y plane than the first absorbent layer.

It is another object of this invention is to provide an absorbent article which utilizes two separate and distinct absorbent members wherein the secondary absorbent member includes one or more areas of low density, such as an aperture, which allows visual inspection of the primary absorbent member.

Other objects and advantages of the present invention will become more apparent to those skilled in the art in view of the following description and the accompanying drawings.

DETAILED DESCRIPTION OF THE PREFERRED EMBODIMENTS

Figure 1:
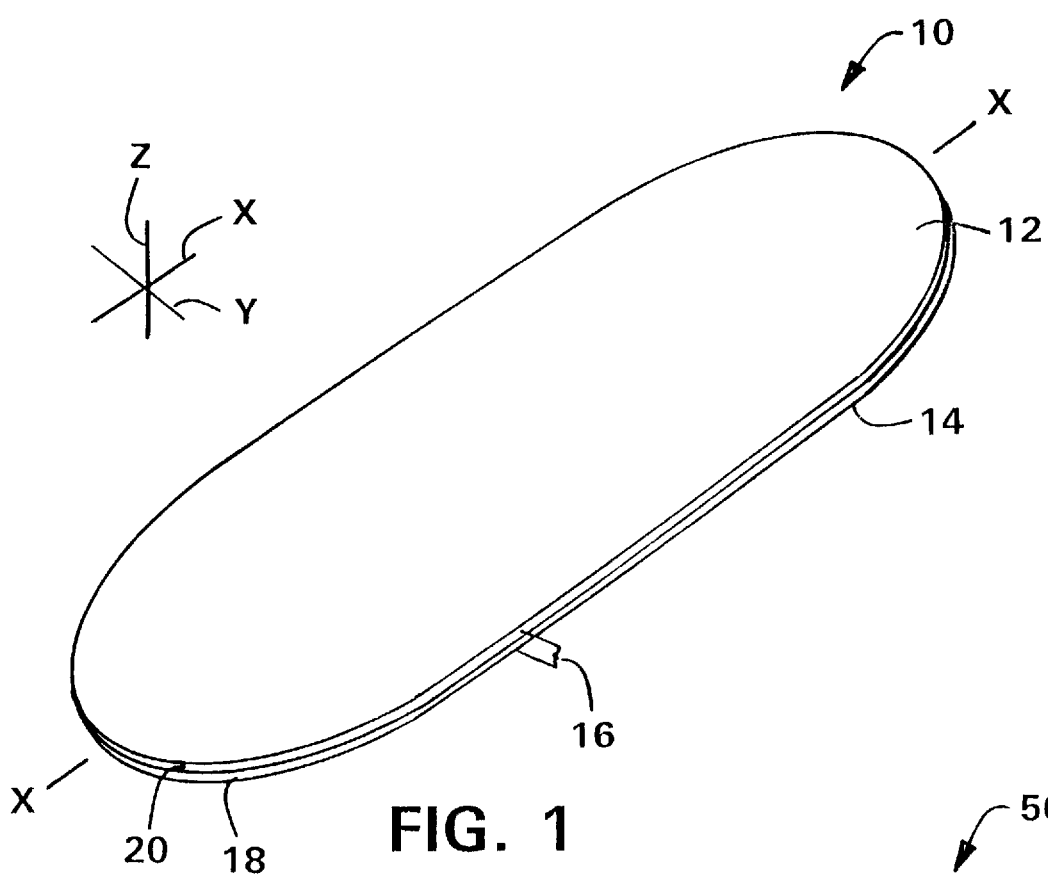
FIG. 1 is a perspective view of the invention illustrated as a sanitary napkin.

Referring to FIG. 1, an absorbent article 10, in the form of a sanitary napkin, is shown which can be worn by a female to absorb body fluids such as menses, blood, urine, and other excrements discharged during a menstrual period. The absorbent article 10 can have a length of about 150 millimeters (mm) to about 300 mm and a width of about 50 mm to about 150 mm. The sanitary napkin 10 has an oval shape. Other shapes including hourglass, dog bone, and racetrack are contemplated to be within the scope of this invention. In a preferred embodiment, the absorbent article 10 can have a caliper or thickness of less than about 15 mm, preferably less than about 10 mm, and most preferably less than about 5 mm.

The absorbent article 10 includes a liquid permeable bodyside cover 12, a liquid-impermeable baffle 14, and an absorbent core 16 positioned between the cover 12 and the baffle 14. The liquid-permeable cover 12 is designed to contact the body of the wearer and can be constructed of a woven or nonwoven, natural or synthetic material which is easily penetrated by body fluids. Suitable materials include bonded carded webs of polyester, polypropylene, polyethylene, nylon or other suitable bondable fibers. Other polyolefins, such as copolymers of polypropylene and polyethylene, linear low density polyethylene, finely perforated film webs and net material also work well. Particularly preferred are composite materials of a polymer and nonwoven fabric material. To facilitate migration of body fluids into the absorbent core 16, the cover 12 can include apertures (not shown). Such apertures can be arranged along the longitudinal central axis X—X if desired and are intended to increase the rate at which body fluids can penetrate down into the absorbent core 16. When apertures are present, body fluid which is deposited at or near the apertures rapidly migrates into the absorbent core 16. This helps maintain a perceivably drier surface than when the apertures are not employed. Therefore, while the apertures are not essential, some functional advantages are obtained in their use.

The liquid-permeable cover 12 can also be treated with a surfactant to make it more hydrophilic and thereby aid in the absorption of the liquid. This surfactant can include typical additions or applied materials like polysiloxine.

The liquid-impermeable baffle 14 is designed to be positioned distally from the cover 12 and generally face the inner surface, i.e., the crotch portion, of an undergarment (not shown). The baffle 14 may permit the passage of air or vapor out of the sanitary napkin 10 while blocking the passage of body fluids in liquid. The baffle 14 can be made from a micro-embossed polymeric film which is polyethylene or polypropylene, or it can be made from bicomponent film. A preferred material is a polyethylene film having a thickness of 0.025 mm to about 0.15 mm.

As shown, the liquid-permeable cover 12, the liquid-impermeable baffle 14, and the absorbent core 16 are coextensive. Alternatively, the cover 12 and baffle 14 can in combination enclose the absorbent core 16. The cover 12 and baffle 14, in those areas where they are in face-to-face contact, can be adhered using any suitable method that does not leave a hard, uncomfortable residue which would be annoying to the wearer. Typical sealing methods include heat sealing, adhesive sealing and ultrasonically bonding on a line outward from the edge of the absorbent core 16 to form a fringe of material. This results in a neat bond line with less tendency for the material to be perforated than by heat sealing.

The absorbent core 16 comprises a primary absorbent member 18 and a secondary absorbent member 20. The primary absorbent member 18 and secondary absorbent member 20 can be joined together in a substantially parallel and coextensive alignment, so that a major face of the primary absorbent member 18 is brought into intimate contact with a major face of the secondary absorbent member 20 thereby allowing the primary absorbent member 18 and secondary absorbent member 20 to be in liquid communication. The primary absorbent member 18 generally has a fluid distribution rate along an X-Y direction greater than about 1.8 times faster than the fluid distribution rate of the secondary absorbent member 20, preferably the fluid distribution rate of the primary absorbent member 18 is greater than about 2 times faster than the fluid distribution rate of the secondary absorbent member 20, and more preferably the fluid distribution rate of the primary absorbent member 18 is greater than about 3 times faster than the fluid distribution rate of the secondary absorbent member 20. The fluid distribution rate is expressed as the ratio of a stain area in the primary absorbent member 18 to the stain area in the secondary absorbent member 20 five minutes after a given volume of test fluid, typically bovine blood, insults the absorbent core 16.

The primary absorbent member 18 is an uncreped throughdried towel (UCTAD) having a basis weight ranging from about 30 grams per square meter to about 120 grams per square meter. Generally, the primary member of the present invention is prepared by a process as disclosed in U.S. Pat. No. 5,048,589 issued to Crook et al. on Sep. 17, 1991; U.S. Pat. No. 5,399,412 issued to Sudall et al. on Mar. 21, 1995; and U.S. Ser. No. 08/447578 filed on May 23, 1995, each commonly assigned to the Kimberly-Clark Corporation, the entire disclosure of each is incorporated herein and made a part hereof. Generally, the process includes the steps of forming a furnish of cellulosic fibers, water, and a chemical debonder; depositing the furnish on a traveling forming belt thereby forming a fibrous web on top of the traveling belt; subjecting the fibrous web to noncompressive drying to remove water from the fibrous web and removing the dried fibrous web from the traveling forming belt. The uncreped throughdried tissue comprising the primary absorbent member 18 possesses a high level of absorbent capacity, absorbency rate, strength, and softness. In a preferred embodiment, the primary absorbent member 18 has a dry tensile strength of less than about 11,000 grams, preferably less than 6,000 grams, and more preferably less than about 2,200 grams. In a particularly preferred embodiment, the primary absorbent member 18 is an uncreped throughdried towel having a wet-to-dry tensile strength ratio greater than about 0.1. The wet/dry ratio is simply the ratio of the wet tensile strength divided by the dry tensile strength. It can be expressed using the machine direction tensile strength, the cross machine direction tensile strength, or the geometric mean tensile strength.

The primary absorbent member 18 can be embossed or apertured (not shown) to lessen the stiffness of the UCTAD towel. Methods for embossing or aperturing the primary absorbent member 18 are known to those skilled in the art. When the primary absorbent member 18 has a plurality of apertures the size of the openings should not exceed 2 millimeters in diameter since this may effect the capacity of the primary absorbent member 18 to absorb fluid exudates or its ability to effectively utilize the capacity of the primary absorbent member 18. Preferably, the apertures are less than 1 millimeter in diameter, and more preferably they are less than 0.5 millimeters. In addition to the size of the apertures, it is important that the total open surface area of the apertures should not exceed 40 percent of the surface area of the primary absorbent member 18 disposed toward the cover 12. Other geometric configurations, such as square, rectangular, triangular, etc., can be used for the apertures.

The secondary absorbent member 20 is a blend of meltblown fiber and staple fibers generally known as coform. Basically the method of manufacturing coform involves extruding a molten nonabsorbent polymeric material through a die head into fine streams and attenuating the streams by converging flow of high velocity heated gas supplied from the nozzles to break the polymer streams into discontinuous microfibers of small diameter. In general, the resulting microfibers have an average fiber density diameter of up to about 10 microns. This primary gas stream is merged with a secondary gas streaming containing individualized wood pulp fibers so as to integrate the two different fibers into a single step. A wide variety of thermoplastic polymers is useful in forming the meltblown microfibers. Such thermoplastic polymers include polyolefins such as polypropylene, polyethylene, polyamides, polyesters, and thermoplastic elastomers such as polyurethane. The process is described in greater detail in U.S. Pat. No. 4,100,324 issued to Anderson et al. on Jul. 11, 1978, and assigned to the common assignee, the disclosure of which is incorporated herein and made a part hereof. It is critical to the invention that a substantial portion of the secondary absorbent member be composed of the nonabsorbent polymeric composition. Preferably, the secondary absorbent member 20 is composed of from about 50 percent to about 95 percent of the nonabsorbent polymeric composition, more preferably it is composed from about 50 percent to about 80 percent of the nonabsorbent polymeric composition and most preferably from about 50 percent to about 75 percent of the nonabsorbent polymeric composition. Desirably, the secondary absorbent member 20 has an average density ranging from about 0.015 grams per cubic centimeter to about 0.1 grams per cubic centimeter and preferably from about 0.02 grams per cubic centimeter to about 0.09 grams per cubic centimeter. It has been discovered that when the nonabsorbent polymeric composition is less than about 50 percent fluid insulting the cover and migrating down will be absorbed into the slower wicking secondary absorbent member 20. Thus, resulting in the problems described above, as well as, reducing the effectiveness and utilization of the absorbent core 16.

The sanitary napkin 10 can include a transfer layer (not shown). The transfer layer is designed to facilitate the movement of fluid downward from the cover and provide a means for separating the cover 12 from the absorbent core 16 to provide a dry sensation and additional comfort to the user. The transfer layer, if used, is preferably positioned between the cover 12 and the second absorbent member 20 and can be configured to correspond to the absorbent core 16. A description of a transfer layer is taught in U.S. Pat. No. 4,798,603 issued to Meyer et al. and assigned to the present assignee. This patent is incorporated herein and made a part hereof.

Figure 2:
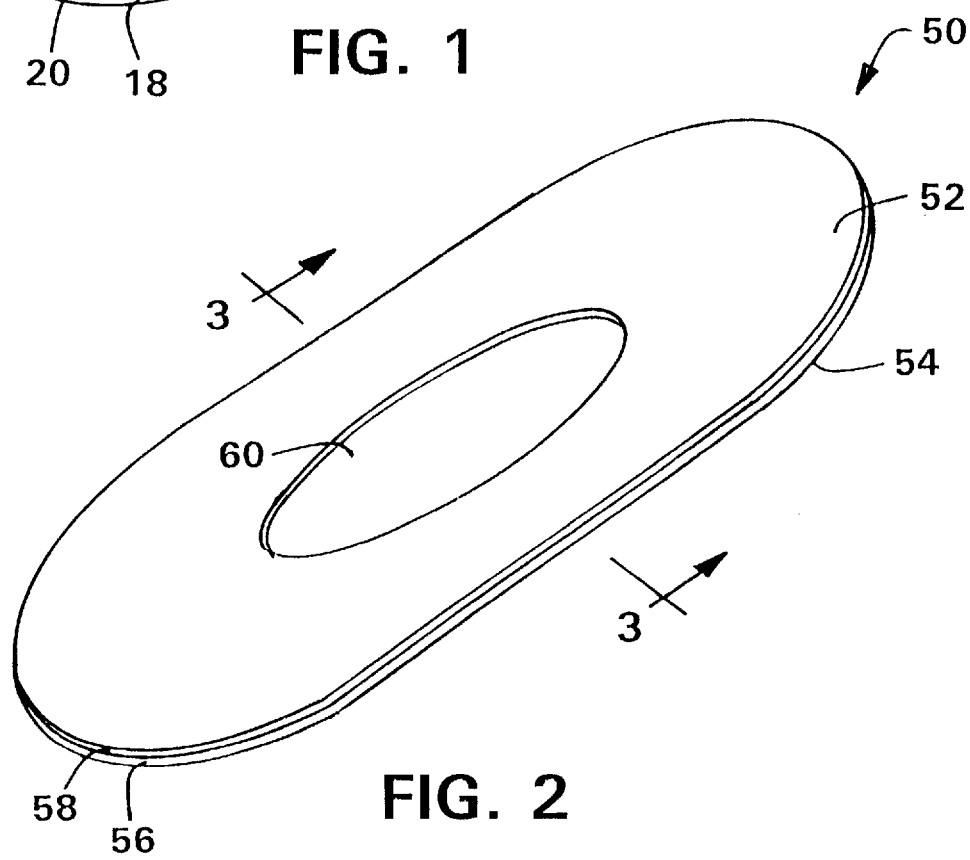
FIG. 2 is another embodiment of a sanitary napkin of this invention having an aperture medially positioned on a sanitary napkin.

Referring to FIG. 2, the absorbent article 50 is depicted as having a cover 52, a baffle 54, a primary absorbent member 56, and a secondary absorbent member 58. The secondary absorbent member 58 has a predetermined surface area disposed toward the cover 52. The secondary absorbent member 58 includes an area 60 having a lower density than the surrounding secondary absorbent member 58 or the primary absorbent member 56. The area 60 can have a density of less than about 0.01 grams per cubic centimeter and preferably less than 0.005 grams per cubic centimeter. Desirably, the area 60 is an aperture or cavity. Desirably, the aperture 60 is appropriately configured and dimensioned so as to allow the wearer to visually inspect the primary absorbent member 56. Accordingly, relative to the secondary absorbent member 58, the aperture 60 can have an open surface greater than about 20 percent, preferably greater than 30 percent and most preferably greater than 50 percent, of the surface area of the secondary absorbent member 58 disposed toward the cover 52. The aperture 60 extends through the secondary absorbent member 58 thereby exposing the primary absorbent member 56. This allows for rapid fluid absorption into the primary absorbent member 56 and for visual inspection of the primary absorbent member 56.

Figure 3:
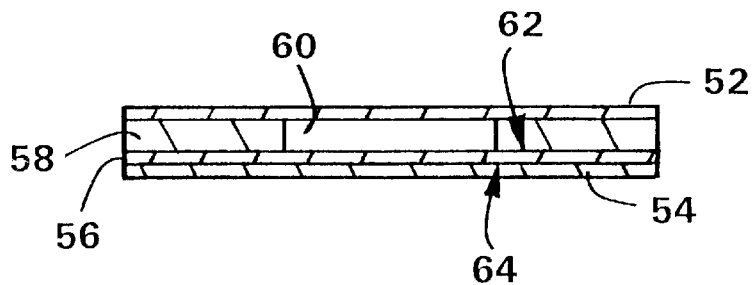
FIG. 3 is a cross-sectional view of the pad shown in FIG. 2 taken along line 3—3.
Figure 3A:
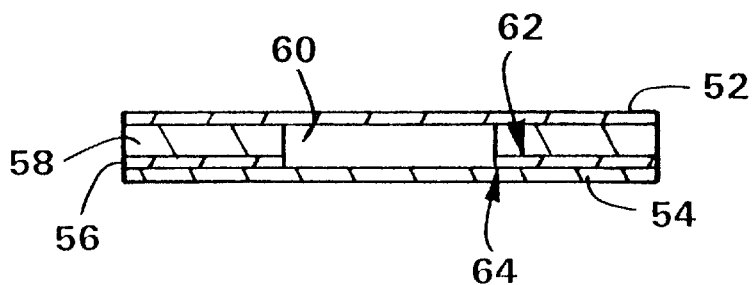
FIG. 3A is a cross-sectional view of another embodiment of the invention.

Referring to FIG. 3A, the aperture 60 can extend through the primary absorbent member 56 and the secondary absorbent member 58. This permits a very rapid fluid acquisition into the sanitary napkin 50. Advantageously, this further allows the sanitary napkin 50 to have a bottom-up filling fluid acquisition, thereby reducing rewet. This embodiment further displays increased absorbent utilization by allowing body fluids to be absorbed into the primary absorbent member 56 without having to desorb fluid from the secondary absorbent member 58.

Referring to FIG. 3, adjacent major faces 62 and 64 define adjacent major surfaces of the primary absorbent member 56 and the secondary absorbent member 58, respectively. The surfaces 62 and 64 can be bonded together by point bonds to form a unitary structure or can be bonded together using other means known in the art such as construction adhesives that are known to those skilled in the art. The major surfaces 62 and 64 are secured together in a manner that will not occlude the fluid flow through the secondary absorbent member 58 or result in a stiff, uncomfortable product.

Figure 4:
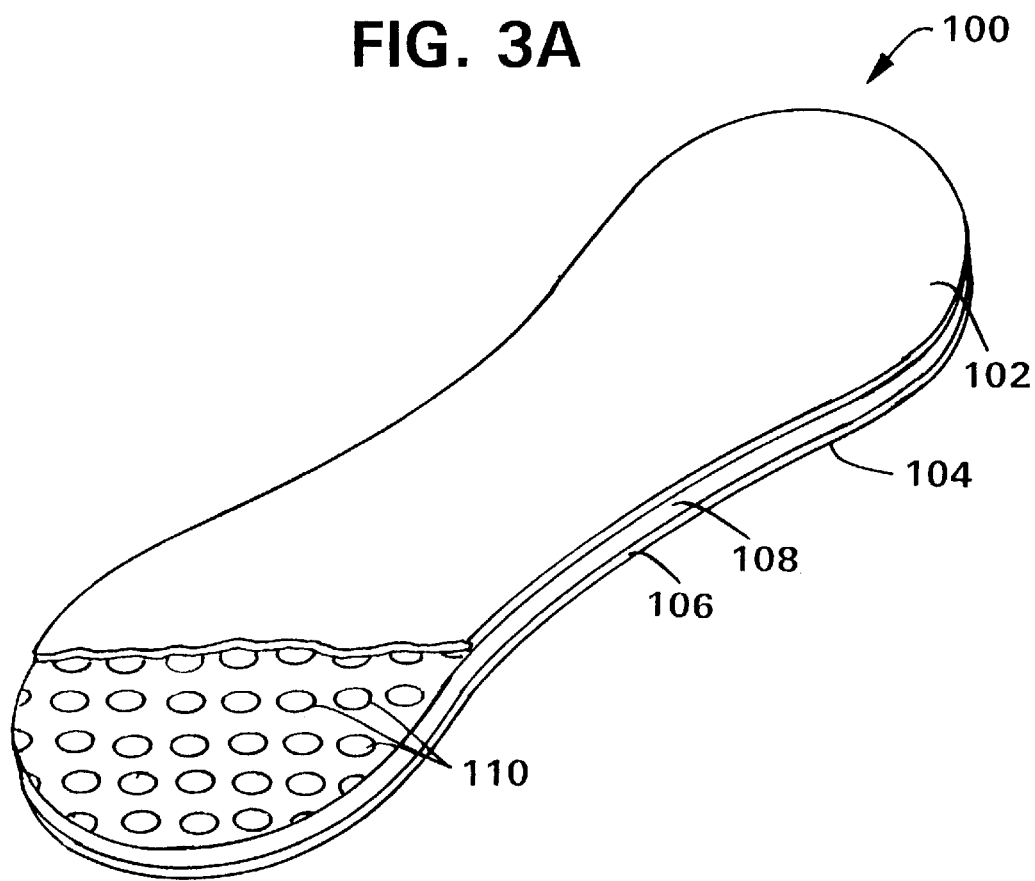
FIG. 4 is a cutaway sectional view of a pad having an hourglass shape with a plurality of apertures below the cover for rapid fluid migration.

Referring to FIG. 4, an absorbent article 100 is shown which contains a cover 102, a baffle 104, a primary absorbent member 106, and a secondary absorbent member 108. The secondary absorbent member 108 includes a plurality of low density areas 110. Preferably the low density areas 110 are apertures or cavities having a diameter greater than about 3 millimeters which extend through the secondary absorbent member 108 to expose the primary absorbent member 106. The apertures 110 have a combined open surface area greater than about 20 percent, preferably greater than about 30 percent, more preferably greater than about 50 percent, relative to the total surface area of the secondary absorbent member 108 disposed toward the cover 102.

The sanitary napkin 10, 50 and 100 can include lateral extensions, (not shown) generally known to those skilled in the art as wings, tabs and panels. The wings are designed to wrap around the outer surface of the crotch portion of a user's undergarment. Typically, at least one of the wings has an adhesive strip attached to one surface, preferably it is the upper surface of one wing. To protect the adhesive from prematurely or inadvertently adhering to a surface prior to the intended use, the adhesive can be covered by a releasable peel strip.

In accordance with the invention, the following examples are being presented for the purpose of illustration only. In the examples, the absorbency of the sanitary napkin was determined by laying the product on a flat level surface. The functionality of the absorbent was evaluated by measuring the surface area of the top and bottom stains of the composites.

The materials used in evaluating the functionality include a 20 cc syringe, an acrylic block further described herein for targeting the test fluid onto the absorbent article, a stopwatch, and bovine blood, available from Cocalico Biologicals, Inc., Stevens Road, Reamstown, Pa. 17567, which was used as the test fluid. The acrylic block measures 4 inches wide×4 inches long and has a thickness of 1 inch. A oval opening measuring ½ inch wide×2 inches long is provided in the center of the block. An indicator mark is positioned at the center on both sides of the opening. The indicator mark assists the placement of the syringe and delivery of the test fluid.

The test method used in evaluating the sanitary napkins involves first conditioning the sanitary napkin by leaving it in a room which is at 21 °±1° C. and at 50±2% relative humidity for a period of two hours. The block was then placed on the center of the pad with the long portion of the opening parallel with the longitudinal edge of the pad. The test quantity of bovine blood was drawn up into the syringe and was dispensed, at the indicator mark, into the opening at a rate of approximately 0.6–0.7 milliliters per second. A total of 6 cubic centimeters (cc) of bovine blood was used to insult the absorbent articles in Examples 1–24. The results of these absorbent article appears in Table 1(Comparative Examples), and Table 2. A total of 10 cc of bovine blood was used to insult the absorbent articles in Examples 25–48. The results of these absorbent article appears in Table 3 (Comparative Examples), and Table 4. When the opening was void of test fluid, the block was removed and wiped clean in preparation for the next pad to be tested. After 5 minutes, the layers of the insulted pad were carefully separated and the area of stain was measured on each absorbent layer.

Bovine blood used in the test has a hematocrit of 33 to 47, a specific gravity of 1.046 to about 1.058, a percent solids of about 19.1 and a colloid osmotic pressure of about 260 to about 300 millimeters of water.

COMPARATIVE EXAMPLES 1–10

Commercially available product was tested in accordance with the method described above. Referring to Table 1, the area of the stain for a 6 milliliter insult of bovine blood was measured after 5 minutes.

TABLE 1

| Sample | Description | Top | Bottom | Ratio |
|---|---|---|---|---|
| 1 | Always ® Ultra Maxi[1] | 6.30 | 5.27 | 0.82 |
| 2 | New Freedom ® Ultra Thin Pads With StayPut Tabs[2] | 5.55 | 3.02 | 0.54 |
| 3 | Always ® Maxi Fluff[1] | 1.89 | 1.48 | 0.78 |
| 4 | Sure & Natural ® Ultra Thin[3] | 3.49 | 3.27 | 0.94 |
| 5 | Stayfree ® Ultra Thin[3] | 5.85 | 3.86 | 0.66 |
| 6 | Kotex ® Maxi Pads[2] | 3.02 | 0.1 | 0.03 |
| 7 | New Freedom ® Maxi Pads[2] | 8.3 | 0.1 | 0.01 |
| 8 | New Freedom ® Thin Pads[2] | 3.5 | 2.76 | 0.79 |
| 9 | Kotex ® Thin Pads[2] | 5.98 | 5.19 | 0.87 |
| 10 | New Freedom ® Ultra Thin Pads[2] | 5.93 | 3.71 | 0.63 |

[1]Available from Procter & Gamble, Cincinnati, OH 45202.
[2]Available from Kimberly-Clark Corp., Neenah, WI 54956.
[3]Available from Personal Product Co., Milltown, NJ 08850

Four test codes were made in accordance with the teachings of Hirt et al., U.S. Pat. No. 5,454,800. Two samples of each code were tested in accordance with the method described above. Referring to Table 2, the area of the stain for a 6 milliliter insult of bovine blood was measured after 5 minutes.

Code 1 included four layers. The first layer was a 5 inch by 8 inch (width×length) 0.8 osy spunbond cover material. The second layer was a 3 inch by 7 inch 100 gsm 60/40 (pulp/polymer) coform material. The third layer was an "e-folded" 35 gsm tissue having a final dimension of 1.5 inch by 7 inch. The fourth and final layer was a 5 inch by 8 inch 1 mil (0.001 of an inch) polyethylene baffle.

Code 2 included four layers. The first layer was a 5 inch by 8 inch 0.8 osy spunbond cover material. The second layer was a 5 inch by 8 inch 100 gsm 60/40 coform material. The third layer was an "e-folded" 35 gsm tissue having a final dimension of 1.5 inch by 7 inch. The fourth and final layer was a 5 inch by 8 inch 1 mil (0.001 of an inch) polyethylene baffle.

Code 3 included four layers. The first layer was a 5 inch by 8 inch 0.8 osy spunbond cover material. The second layer included two spaced apart strips of 100gsm, 60/40 coform material having a final dimension of 3 inches by 7 inches with a one-eight of an inch separation. The third layer was an "e-folded" 35 gsm tissue having a final dimension of 1.5 inch by 7 inch. The fourth and final layer was a 5 inch by 8 inch 1 mil (0.001 of an inch) polyethylene baffle.

Code 4 included five layers. The first layer was a 5 inch by 8 inch 0.8 osy spunbond cover material. The second layer was a 1.25 inch by 7 inch 60 gsm meltblown material. The third layer was three spaced apart strips of 100 gsm, 60/40 coform material having a final dimension of 3 inches by 7 inches with a one-eight of an inch separation between the strips. The fourth layer was an "e-folded" 35 gsm tissue having a final dimension of 1.5 inch by 7 inch. The fifth and final layer was a 5 inch by 8 inch 1 mil (0.001 of an inch) polyethylene baffle.

TABLE 2

| Code | Top Stain Area (in$^2$) | Bottom Stain Area (in$^2$) | Stain Ratio (Bottom/Top) |
|---|---|---|---|
| 1 | 6.5 | 6.4 | 0.985 |
|   | 6.7 | 6.7 | 1.000 |
| 2 | 5.5 | 6.7 | 1.218 |
|   | 5.2 | 6.1 | 1.173 |
| 3 | 5.9 | 5.7 | 0.966 |
|   | 6.7 | 6.1 | 0.910 |
| 4 | 6.4 | 5.4 | 0.844 |
|   | 6.4 | 6.9 | 1.078 |

EXAMPLES 11–24

Referring to Table 3, which is illustrative of the present invention, stain dimensions for a 6 millimeter insult of bovine blood after 5 minutes is shown. The test absorbent core of the sanitary napkin measured 178 millimeters in length and 76 millimeters in width.

TABLE 3

| Sample | Description | Top | Bottom | Ratio |
|---|---|---|---|---|
| 11 | 2 layers of 135 gsm coform * having a 24 mm × 62 mm center aperture and 2 layers of 105 gsm UCTAD towel. | 1.76 | 5.32 | 3.02 |
| 12 | 2 layers of 135 gsm coform and 2 layers of 105 gsm UCTAD towel. | 1.15 | 5.28 | 4.59 |
| 13 | 2 layers of 135 gsm coform having a 24 mm × 62 mm center aperture and 2 layers of 105 gsm UCTAD towel. | 2.10 | 6.20 | 2.86 |
| 14 | 2 layers of 135 gsm coform and 3 layers of 60 gsm UCTAD towel. | 1.61 | 4.62 | 2.87 |
| 15 | 1 layer of 135 gsm coform; 1 layer of 225 gsm cellulose pulp paper that is microstrained and 2 layers of 105 gsm UCTAD towel. | 1.49 | 3.90 | 2.63 |
| 16 | 1 layer of 135 gsm coform and 1 layer of 225 gsm cellulose pulp paper that is microstrained each having a 24 mm × 62 mm center aperture and 3 layers of 60 gsm UCTAD towel. | 2.73 | 5.83 | 2.14 |
| 17 | 1 layer of 135 gsm coform; 1 layer of 225 gsm cellulose pulp paper that is microstrained; and 3 layers of 60 gsm UCTAD towel. | 1.87 | 5.59 | 2.99 |
| 18 | 2 layers of 135 gsm coform having a 24 mm × 62 mm center aperture and 225 gsm cellulose pulp paper that is microstrained. | 5.23 | 8.46 | 1.62 |
| 19 | 1 layer of 135 gsm coform and 1 layer of 225 gsm cellulose pulp paper that is microstrained each having a 24 mm × 62 | 2.94 | 5.91 | 2.01 |

TABLE 3-continued

| Sample | Description | Top | Bottom | Ratio |
|---|---|---|---|---|
|  | mm center aperture and 1 layer of 225 gsm cellulose pulp paper that is microstrained. | | | |
| 20 | 1 layer of 225 gsm cellulose pulp paper that is microstrained having a 24 mm × 62 mm center aperture and 2 layers of 105 gsm UCTAD towel. | 6.91 | 6.24 | 0.90 |
| 21 | 1 layer of 135 gsm coform and 1 layer of 225 gsm cellulose pulp paper that is microstrained each having a 24 mm × 62 mm center aperture and 2 layers of 105 gsm UCTAD towel. | 2.57 | 5.93 | 2.31 |
| 22 | 2 layers of 135 gsm coform having a 24 mm × 62 mm center aperture and 6 layers of 60 gsm UCTAD towel. | 2.07 | 7.04 | 3.40 |
| 23 | 1 layer of 135 gsm coform with a 24 mm × 62 mm center aperture, 2 layers of 60 gsm UCTAD each with a 24 mm × 64 mm center aperture, 1 layer of 135 gsm coform with a 24 mm × 62 mm center aperture and 2 layers of 60 gsm UCTAD towel. | 1.93 | 7.71 | 3.99 |
| 24 | 1 layer of 135 gsm coform with a 24 mm × 62 mm center aperture, 3 layers of 60 gsm UCTAD towel each with a 24 mm × 64 mm center aperture, and 3 layers of 60 gsm UCTAD towel. | 2.26 | 8.62 | 3.81 | coform composition was 60:40 polymer to pulp ratio.

COMPARATIVE EXAMPLES 25–34

Commercially available product was tested in accordance with the method described above. Referring to Table 4, the area of the stain for a 10 milliliter insult of bovine blood was measured after 5 minutes.

TABLE 4

| Sample | Description | Top | Bottom | Ratio |
|---|---|---|---|---|
| 25 | Always ® Ultra Maxi | 10.6 | 9.99 | 0.94 |
| 26 | New Freedom ® Ultra Thin Pads With Stayput Tabs | 7.95 | 5.78 | 0.72 |
| 27 | Always ® Maxi Fluff | 2.71 | 2.94 | 1.08 |
| 28 | Sure & Natural ® Ultra Thin | 5.62 | 6.2 | 1.10 |
| 29 | Stayfree ® Ultra Thin | 8.06 | 8.39 | 1.04 |
| 30 | Kotex ® Maxi Pads | 3.76 | 0.1 | 0.03 |
| 31 | New Freedom ® Maxi Pads | 5.98 | 2.17 | 0.36 |
| 32 | New Freedom ® Thin Pads | 4.51 | 5.32 | 1.18 |
| 33 | Kotex ® Thin pads | 7.17 | 7.17 | 1.00 |
| 34 | New Freedom ® Ultra Thin Pads | 10.97 | 8.86 | 0.81 |

Two samples of the four test codes described above were tested in accordance with the method described above. Referring to Table 5, the area of the stain for a 10 milliter insult of bovine blood was measured after 5 minutes.

TABLE 5

| Code | Top Stain Area (in$^2$) | Bottom Stain Area (in$^2$) | Stain Ratio (Bottom/Top) |
|---|---|---|---|
| 1 | 10.5 | 7.5 | 0.714 |
|  | 10.1 | 7.3 | 0.723 |
| 2 | 8.2 | 9.6 | 1.171 |
|  | 9.1 | 10 | 1.099 |
| 3 | 10.6 | 7.9 | 0.745 |
|  | 10.4 | 8.3 | 0.798 |
| 4 | 7.2 | 7.8 | 1.083 |
|  | 7.8 | 7.5 | 0.962 |

EXAMPLES 35–48

Referring to Table 6, which is illustrative of the present invention, stain dimensions for a 10 millimeter insult of bovine blood after 5 minutes are shown.

TABLE 6

| Sample | Description | Top | Bottom | Ratio |
|---|---|---|---|---|
| 35 | 2 layers of 135 gsm coform * having a 24 mm × 62 mm center aperture and 2 layers of 105 gsm UCTAD towel. | 2.73 | 7.6 | 2.78 |
| 36 | 2 layers of 135 gsm coform and 2 layers of 105 gsm UCTAD towel. | 2.99 | 8.22 | 2.75 |
| 37 | 2 layers of 135 gsm coform having a 24 mm × 62 mm center aperture and 2 layers of 105 gsm UCTAD towel. | 2.98 | 10.72 | 3.60 |
| 38 | 2 layers of 135 gsm coform and 3 layers of 60 gsm UCTAD towel. | 2.24 | 7.71 | 3.44 |
| 39 | 1 layer of 135 gsm; 1 layer of 225 gsm cellulose pulp paper that is microstrained and 2 layers of 105 gsm UCTAD towel. | 2.81 | 7.57 | 2.69 |
| 40 | 1 layer of 135 gsm coform and 1 layer of 225 gsm cellulose pulp paper that is microstrained each having a 24 mm × 62 mm center aperture and 3 layers of 60 gsm UCTAD towel. | 3.69 | 9.25 | 2.51 |
| 41 | 1 layer of 135 gsm coform; 1 layer of 225 gsm cellulose pulp paper that is microstrained; and 3 layers of 60 gsm UCTAD towel. | 3.25 | 8.36 | 2.57 |
| 42 | 2 layers of 135 gsm coform having a 24 mm × 62 mm center aperture and 225 gsm cellulose pulp paper that is microstrained. | 4.73 | 12.57 | 2.66 |
| 43 | 1 layer of 135 gsm coform and 1 layer of 225 gsm cellulose pulp paper that is microstrained each having a 24 mm × 62 mm center aperture and 1 layer of 225 gsm cellulose pulp paper that is microstrained. | 4.58 | 9.18 | 2.00 |
| 44 | 1 layer of 225 gsm cellulose pulp paper that is microstrained having a 24 mm × 62 mm center aperture and 2 layers of 105 gsm UCTAD towel. | 9.76 | 8.89 | 0.91 |
| 45 | 1 layer of 135 gsm coform and 1 layer of 225 gsm cellulose pulp paper that is microstrained each having a 24 mm × 62 mm center aperture and 2 layers of 105 gsm UCTAD towel. | 3.62 | 8.47 | 2.34 |
| 46 | 2 layers of 135 gsm coform having a 24 mm × 62 mm center aperture and 6 layers of 60 gsm UCTAD towel. | 3.84 | 9.25 | 2.41 |
| 47 | 1 layer of 135 gsm coform with a 24 mm × 62 mm center aperture, 2 layers of 60 gsm UCTAD each with a 24 mm × 64 mm center aperture, 1 layer of 135 gsm coform with a 24 mm × 62 mm center aperture and 2 layers of 60 gsm UCTAD towel. | 1.68 | 5.09 | 3.03 |
| 48 | 1 layer of 135 gsm coform with a 24 mm × 62 mm center aperture, 3 layers of 60 gsm UCTAD towel each with a 24 mm × 64 mm center aperture, and 3 layers of 60 gsm UCTAD towel. | 2.96 | 11.25 | 3.80 |

While the invention has been described in conjunction several specific embodiments, it is to be understood that many alternatives, modifications, and variations will be apparent to those skilled in the art in light of the foregoing description. Accordingly, this invention is intended to embrace all such alternatives, modifications and variations which followed in the spirit and scope of the appended claims.

We claim:

1. An absorbent article having an absorbent core comprising a primary absorbent member and a secondary absorbent member superposed over a portion of said primary absorbent member, said primary absorbent member has a distribution rate of bovine blood along an X-Y direction greater than about 1.8 times faster than said secondary absorbent member.

2. The absorbent article of claim 1 wherein said secondary absorbent member is composed of from about 50% to about 95% of said non-absorbent polymeric composition.

3. The absorbent article of claim 1 wherein said primary absorbent member has a fluid distribution rate greater than about 2 times faster than said secondary absorbent member.

4. The absorbent article of claim 1 wherein said primary absorbent member has a fluid distribution rate greater than about 3 times faster than said secondary absorbent member.

5. The absorbent core of claim 1 wherein said primary absorbent member and said secondary absorbent member have coterminous outer perimeters.

6. The absorbent core of claim 1 wherein said secondary absorbent member has an aperture extending through said secondary absorbent member.

7. The absorbent core of claim 1 wherein said non-absorbent polymeric composition is selected from polyethylene, polypropylene, polyesters, and mixtures thereof.

8. The absorbent core of claim 1 wherein said secondary absorbent member has an average density ranging from about 0.015 grams per cubic centimeter to about 0.1 grams per cubic centimeter.

9. The absorbent core of claim 1 wherein said primary absorbent member is an uncreped throughdried towel having a basis weight ranging from about 30 grams per square meter to about 120 grams per square meter.

10. The absorbent core of claim 6 wherein said aperture has a diameter greater than about 3 millimeters.

11. The absorbent core of claim 9 wherein said primary absorbent member includes an aperture.

12. An absorbent article having an absorbent core comprising a primary absorbent member and secondary absorbent member comprising from about 50% to about 95% of a non-absorbent polymeric composition superposed over a portion of said primary absorbent member wherein said primary absorbent member has a distribution rate of bovine blood along an X-Y direction greater than about 1.8 times faster than said secondary absorbent member.

13. The absorbent article of claim 12 wherein said primary absorbent member is an uncreped throughdried towel.

14. The absorbent article of claim 12 wherein said primary absorbent member and said secondary absorbent member have coterminous outer perimeters.

15. The absorbent article of claim 12 wherein said secondary absorbent member includes an aperture extending through said secondary absorbent member, said aperture having an open area greater than about 20%.

16. The absorbent core of claim 13 wherein said uncreped throughdried towel has a basis weight ranging from about 45 grams per square meter to about 120 grams per square meter.

17. A sanitary napkin having a thickness of less than about 5 millimeters with an absorbent core comprising a primary absorbent member and a secondary absorbent member positioned immediately adjacent to and superposed over a portion of said primary absorbent member, wherein said primary absorbent member is an uncreped throughdried towel having a basis weight ranging from about 30 grams per square meter to about 120 grams per square meter, said secondary absorbent member being composed of from about 50% to about 95% of a non-absorbent polymeric composition and having an average density ranging from about 0.015 grams per cubic centimeter to about 0.1 grams per cubic centimeter and wherein said primary absorbent member has a fluid distribution rate of bovine blood along an X-Y direction greater than about 1.8 times faster than said secondary absorbent member.

18. The absorbent core of claim 17 wherein said primary absorbent member is an uncreped throughdried towel having a wet to dry tensile strength ratio greater than about 0.1.

19. The absorbent article of claim 17 wherein said secondary absorbent member includes an aperture extending through said secondary absorbent member, said aperture having an open area greater than about 30%.

20. The absorbent core of claim 17 wherein said non-absorbent polymeric composition is selected from polyethylene, polypropylene, polyesters, and mixtures thereof.

* * * * *

UNITED STATES PATENT AND TRADEMARK OFFICE
CERTIFICATE OF CORRRECTION

PATENT NO. : 5,810,798
DATED : Sept. 22, 1998
INVENTOR(S) : Finch, et al.

Page 1 of 2

It is certified that error appears in the above-identified patent and that said Letters Patent is hereby corrected as shown below:

On the title page, item [56] insert the following:

FOREIGN PATENT DOCUMENTS

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | CA | 21 | 54 | 9 | 2 | 0 | A1 | 12/31/96 | Canada | | | | |
| | | DE | 19 | 60 | 94 | 6 | 2 | A1 | 09/18/97 | Germany | | | | |
| | | GB | 22 | 93 | 6 | 1 | 1 | A | 04/03/96 | Great Britain | | | | |
| | | WO | 96/ | 06 | 5 | 9 | 1 | A3 | 03/07/96 | World - PCT | | | | |
| | | | | | | | | | | | | | | |

UNITED STATES PATENT AND TRADEMARK OFFICE
CERTIFICATE OF CORRRECTION

PATENT NO. : 5,810,798
DATED : Sept. 22, 1998
INVENTOR(S) : Finch, et al.

Page 2 of 2

It is certified that error appears in the above-identified patent and that said Letters Patent is hereby corrected as shown below:

OTHER DOCUMENTS

|   |   |   |
|---|---|---|
|   | Patent Cooperation Treaty Search Report from the International Search Authority, |
|   | International Application No. PCT/US 98/00621 dated June 4, 1998. |
|   |   |

Signed and Sealed this

Twentieth Day of April, 1999

*Attest:*

Q. TODD DICKINSON

*Attesting Officer*  Acting Commissioner of Patents and Trademarks